(12) United States Patent
Mercier et al.

(10) Patent No.: US 8,518,993 B2
(45) Date of Patent: Aug. 27, 2013

(54) COMBINATION OF BIOAVAILABLE METHIONINE WITH AT LEAST ONE ESSENTIAL OIL

(75) Inventors: Yves Mercier, Clermont-Ferrand (FR); Pierre-André Geraert, Rochecorbon (FR)

(73) Assignee: Adisseo Ireland Ltd., Dublin (IE)

( * ) Notice: Subject to any disclaimer, the term of this patent is extended or adjusted under 35 U.S.C. 154(b) by 484 days.

(21) Appl. No.: 11/991,573

(22) PCT Filed: Sep. 11, 2006

(86) PCT No.: PCT/FR2006/002080
§ 371 (c)(1),
(2), (4) Date: Jun. 4, 2008

(87) PCT Pub. No.: WO2007/031632
PCT Pub. Date: Mar. 22, 2007

(65) Prior Publication Data
US 2009/0048342 A1 Feb. 19, 2009

(30) Foreign Application Priority Data
Sep. 12, 2005 (FR) ..................................... 05 09273

(51) Int. Cl.
*A61K 31/195* (2006.01)
(52) U.S. Cl.
USPC ......................................................... 514/562

(58) Field of Classification Search
None
See application file for complete search history.

(56) References Cited

U.S. PATENT DOCUMENTS

| 4,166,867 | A | 9/1979 | Betz et al. |
| 6,322,825 | B1 * | 11/2001 | Ninkov ........................ 424/745 |
| 6,451,861 | B1 | 9/2002 | Pimentel et al. |
| 6,649,660 | B2 * | 11/2003 | Ninkov ........................ 514/731 |
| 2002/0146399 | A1 | 10/2002 | Raczek |
| 2004/0241194 | A1 | 12/2004 | Picaud et al. |

FOREIGN PATENT DOCUMENTS

| EP | 1 314 358 A1 | 5/2003 |
| EP | 1 314 359 A1 | 5/2003 |
| EP | 1 358 805 | * 11/2003 |
| WO | WO 03/056935 A1 | 7/2003 |

OTHER PUBLICATIONS

Losa (Feed Manufacturing in the Mediterranean Region. Improving Saftey: From Feed to Food. Proceedings of the III Conference of Feed Manufacturers of the Mediterranean, Reus, Spain, Mar. 2000, Cahiers Options Mediterraneennes 54:39-44, 2001).*
Cox et al (Molecules 6:87-91, 2001).*

* cited by examiner

*Primary Examiner* — Craig Ricci
(74) *Attorney, Agent, or Firm* — Oliff & Berridge, PLC

(57) ABSTRACT

The invention concerns a food composition, designed to complement animal feed in methionine, said composition having a synergistic bactericidal effect on the bacterial activity of the bowel flora. Said food composition of bioavailable methionine comprises: a) a bioavailable methionine compound and b) at least one essential oil.

8 Claims, No Drawings

COMBINATION OF BIOAVAILABLE METHIONINE WITH AT LEAST ONE ESSENTIAL OIL

The present invention relates to a feed composition, intended for supplementation of livestock feed with methionine.

The intestinal microflora of animals is composed of various complex communities, comprising bacteria, yeasts and fungi. This microflora has considerable effects on animal health and nutritional efficiency.

Two types of bacteria generally occur: on the one hand the pathogenic bacteria (for example, *Salmonella, Campylobacter jejuni* or *Clostridium perfringens*), and on the other hand, bacteria that are not regarded as pathogenic (for example, *Lactobacillus* or *Propionibacterium*). The overall balance of the effects of these bacteria on livestock performance is negative.

For many years, companies involved in livestock raising have endeavoured to adjust the intestinal bacterial flora in order to improve animal performance.

Notably it is now customary to supplement animal feeding stuffs with growth factor antibiotics, which can lower the total bacterial load of the digestive tract and improve performance in terms of growth or production. However, the use of antibiotics as growth factors has been prohibited in Europe since 1 Jan. 2006.

Therefore there is a perceived need for replacement products.

One aim of the present invention is to offer a composition intended for feeding livestock that has a bactericidal effect on the intestinal flora of the livestock.

Another aim of the present invention is to offer a composition intended for feeding livestock that will have a beneficial effect on the performance of the animals.

Another aim of the present invention is to offer a feed composition which does not contain antibiotics, yet has the beneficial effects that the antibiotics generally have on growth of the animals.

Yet another aim of the present invention is to offer a feed composition that has an action on the intestinal flora of livestock.

The present invention therefore relates to a synergistic feed composition of bioavailable methionine intended as feed for livestock, comprising:
a) a bioavailable methionine compound, and
b) at least one essential oil.

The inventors have noted that the composition of the present invention which comprises these two compounds has a synergistic bactericidal effect on the activity of the intestinal flora. Indeed, the bioavailable methionine compound and the essential oil, or the mixture of essential oils, reinforce the effects of one another.

No prior art document describes the synergistic bactericidal effect of a bioavailable methionine compound and of at least one essential oil.

By "bioavailable methionine", we mean any compound for supplementing the daily requirements of livestock for methionine. In fact, methionine can be supplied to livestock in various forms.

According to the present invention, the bioavailable methionine compound is in the isolated state.

Firstly, it can be methionine itself, notably L-methionine or D,L-methionine.

It can also be a methionine derivative. By "methionine derivative", we mean for example the salts, amides, alkyl and alcoholic esters, ketone derivatives and hydroxy-analogues of methionine and derivatives of them.

It can be 2-hydroxy-4-methylthiobutanoic acid (hereinafter called HMTBA or hydroxy-analogue of methionine), a known methionine analogue for feeding livestock. It has the advantage of being in liquid form, which makes it easier for the animal feed producing companies to use.

It can also be the isopropyl ester of the hydroxy-analogue of methionine, or the tert-butyl ester of methionine.

The feed composition of the invention can also contain several sources of bioavailable methionine, for example a mixture of methionine and its hydroxy-analogue.

The bioavailability of the source of methionine is found by determining the level of the active compound in the blood, relative to the amount of active compound introduced in the feed ration of the animal. This determination takes into account the degree of absorption in the intestine during transit through the digestive tract, passage of the alimentary bolus through the various stomach compartments of animals with a multi-compartment stomach, and the degree of transformation of the active compound by the body (e.g. in the case of the hydroxy-analogue of methionine).

By "essential oil", we mean a liquid obtained from plants (flowers, buds, seeds, leaves, twigs, grasses, peel, wood, fruit and roots). The essential oils can notably be obtained by expression, fermentation, enfleurage or extraction. The essential oils are sometimes called ethereal or volatile oils, owing to the presence of terpenes (non-aromatic carbohydrates) and oxidized compounds (alcohols, aldehydes, ketones) which are aromatic. The essential oil can be raw, depentenized, rectified or composite.

The essential oil can, according to the present invention, be a mixture of essential oils.

According to one embodiment of the present invention, the essential oils are composed to more than 5% of at least one of the compounds selected from linalyl acetate, cuminic alcohol, cinnamic aldehyde, borneol, cadinene, camphene, camphor, carvacrol, carvone, cineol, citral, citronellal, citronellol, cymene, dipentene, estragol, eugenol, geraniol, limonene (D or L), linalool (D or L), menthol, methylchavicol, paracymene, phellandrene, pinene (alpha or beta), methyl salicylate, terpinene (alpha and beta), terpineol (alpha and beta), thuyone, thymol, bornyl acetate, geranyl acetate, eugenyl acetate, cuminic aldehyde, allicine, anethol, perillaldehyde and sabinene. They are more preferably composed to more than 10% of at least one of these compounds.

The oils used are preferably extracted by cold expression of the peel or by distillation of various parts of the following plants: garlic, blueberry, aloe, dill, aniseed, tea tree, basil, bergamot, rosewood, birch, cade, carrot, curcuma, cajeput, camphor, cinnamon, caraway, celery, oak, lemon, citronella, coriander, cumin, estragon, Eucalyptus globulus, fennel, juniper, geranium bourbon, ginger, ginseng, clove, hyssop, true laurel, true lavender, aspic, lemongrass, lime, mandarin, marjoram, peppermint, nutmeg, myrrh, myrtle, cajuput, onion, olibanum, orange, origanum, palmarosa, grapefruit, papaya, paprika, patchouli, parsley, red pepper, maritime pine, Scotch pine, apple, horseradish, rosemary, sandalwood, savory, sassafras, sage, wild thyme, turpentine, red thyme, vervain, vetiver, ylang-ylang.

By "animal", we mean more particularly livestock and notably the grazing animals (notably cattle raised for meat, milk, cheese and leather; sheep raised for meat, wool and cheese; goats; pigs), rabbits, poultry (chicken, hens, turkeys, ducks, geese and others), aquatic animals (for example fish, shrimps, oysters and mussels), animals for leisure activities and pets (notably horse, dog, cat). Cattle, or bovines, constitute a sub-family of the Bovidae, ruminants with a multi-compartment stomach, which includes several important species of livestock animals (milk breeds, meat breeds and mixed breeds).

The composition of the invention is in the form of powder or in the form of liquid. As for the bioavailable methionine, it is in the form of powder or of granules. This also requires dilution of this powder in the essential oil to produce the composition according to the present invention. As described above, methionine can also occur in the form of hydroxy-analogue, and therefore in liquid form. In this case, the two liquids are mixed homogeneously before being administered to the animals or mixed with the animal's feed ration.

Preferably, compound a) is selected from methionine itself (L-methionine or D,L-methionine), or one of its derivatives, such as salt, amide, alkyl and alcoholic ester, ketone derivative, hydroxy-analogue or a derivative of these products.

According to one embodiment of the present invention, compound a) is of the general formula (I):

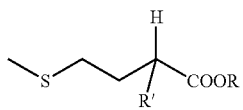

in which
R represents H or an isopropyl group and
R' represents —OH or —NH$_2$.

According to one embodiment of the present invention, the feed additive of the present invention which has a synergistic bactericidal effect on the intestinal flora of the animals, comprises:
  a) from 5 to 95 wt. % of a bioavailable methionine compound,
  b) from 5 to 95 wt. % of at least one essential oil, and
  c) optionally, at least one other compound.

According to this embodiment, the feed composition may comprise at least one other compound, for example an emulsifier or gelatin. According to this embodiment, it is an open composition.

Advantageously, the said composition comprises from 10 to 90 wt. % of a bioavailable methionine compound, from 10 to 90 wt. % of at least one essential oil and, optionally, at least one other compound.

According to yet another embodiment of the present invention, the said composition comprises from 15 to 85 wt. % of a bioavailable methionine compound, from 15 to 85 wt. % of at least one essential oil and, optionally, at least one other compound.

According to another embodiment of the present invention, the said composition comprises from 20 to 80 wt. % of a bioavailable methionine compound, from 20 to 80 wt. % of at least one essential oil and, optionally, at least one other compound.

According to quite another embodiment of the present invention, the feed composition, which has a synergistic bactericidal effect on the intestinal flora of the animals, consists of:
  a) 5 to 95 wt. % of a bioavailable methionine compound, and
  b) 5 to 95 wt. % of at least one essential oil.

According to this embodiment, the feed composition comprises only these two compounds, it contains no other compound. According to this embodiment, it is a closed composition.

Advantageously, the feed composition of the present invention consists of 10 to 90 wt. % of a bioavailable methionine compound and of 10 to 90 wt. % of at least one essential oil.

According to yet another embodiment of the present invention, the said composition consists of 15 to 85 wt. % of a bioavailable methionine compound and of 15 to 85 wt. % of at least one essential oil.

According to another embodiment of the present invention, the said composition comprises from 20 to 80 wt. % of a bioavailable methionine compound, from 20 to 80 wt. % of at least one essential oil and, optionally, at least one other compound.

According to one embodiment of the present invention, the bioavailable methionine (i.e. compound a)) is present in the composition in a proportion greater than 60 wt. %, preferably greater than 80 wt. %.

According to one embodiment of the present invention, the essential oil (i.e. compound b)) is present in the composition in a proportion less than 40 wt. %, preferably less than 20 wt. %, and even more preferably less than 10 wt. %. Moreover, according to one embodiment of the present invention, compound b) is present in the composition in a proportion greater than 5 wt. %, preferably greater than or equal to 8 wt. %.

The present invention also relates to a feed additive comprising the composition according to the present invention.

By "feed additive" is meant an active compound or a mixture of active compounds that go or goes to make up the composition of the feed in a proportion generally less than 2 wt. %, for example less than 1 wt. %, of the feed.

The present invention also relates to an animal feed, notably of the feed ration type, containing the feed composition as defined above or containing the said feed additive.

The present invention finally relates to the use of the composition as defined above, to obtain a feed additive.

According to one embodiment of the present invention, such use may in addition lower the activity of the endogenous flora in livestock or help to combat the harmful effects of the pathogenic microorganisms of the intestinal flora of livestock.

According to one embodiment of the present invention, such use may in addition improve the performance of livestock such as growth, viability, homogeneity, production efficiency.

According to another embodiment of the present invention, the composition improves the performances for a reduction in the activity of the intestinal flora of livestock.

Thus, according to the present invention, the composition of the present invention is used to prepare a feed additive for livestock for improving the performances through a reduction in the activity of the intestinal flora of the said animals.

The examples given below and the figures will illustrate and demonstrate certain advantages and characteristics of the present invention.

The purpose of the following tests is to compare the production of gas by the flora of the ileal contents of meat chicken, in relation to various test parameters. The production of gas is an indirect indicator of the bacterial activity of the ileal flora of the chicken.

EXAMPLE 1

Animals and Samples 50 meat chicken are raised with a wheat-based diet. These chicken are raised with the same nutritional regimen. The chicken are sacrificed on the 35th day, then the contents of their ileum are removed in anaerobic conditions. The contents are placed in bottles which are stored at −18° C.

Tests In Vitro

Based on the experimental design described in Table I below, the volume of gas produced is measured as a function of time.

48 bottles are filled successively with:

the treatment (nothing for the negative control, HMTBA, EO or the test item), 90 ml of buffer solution, containing wheat starch (nutrient medium for the bacteria); the function of this buffer solution is to maintain a constant pH and suppress $O_2$ 10 ml of inoculum, comprising a mixture of ¼ of ileal contents and ¾ of sterile physiological solution, which is filtered and homogenized before filling.

The doses tested are calculated to be representative of the concentrations of the products that would be found in the gastrointestinal contents of the animals.

makes it possible to establish the differences on the means between the various treatments.

Results

The results are shown in Table II below.

In Table II, the values of the parameters are significantly different at the threshold of 5% when the treatments do not have any letter in common.

Firstly, it can be seen that all the compositions tested give results that are significantly different from the control according to the two criteria, namely Vf and Trm. These compositions therefore have a reducing effect on the activity of the ileal flora.

The objective is to maximize Trm. All the test items are therefore effective.

It is demonstrated that there is a synergistic effect between the compound of bioavailable methionine, specifically HMTBA, and the essential oil, on bacterial activity.

TABLE I

| | | Treatment | | | | | | | | | | |
|---|---|---|---|---|---|---|---|---|---|---|---|---|
| | | Negative control | HMTBA | EO 1 | Test item 1 | EO 2 | Test item 2 | EO 3 | Test item 3 | EO 4 | Test item 4 | EO 5 | Test item 5 |
| item | | 0 | HMTBA | EO 1 | HMTBA + EO 1 | EO 2 | HMTBA + EO 2 | EO 3 | HMTBA + EO 3 | EO 4 | HMTBA + EO 4 | EO 5 | HMTBA + EO 5 |
| repetitions | | 4 | 4 | 4 | 4 | 4 | 4 | 4 | 4 | 4 | 4 | 4 | 4 |
| dose of HMTBA supplied | mg wt. % | 0 0 | 83 100 | 0 0 | 83 75 | 0 0 | 83 62.5 | 0 0 | 83 71.4 | 0 0 | 83 73 | 0 0 | 83 62.5 |
| dose of EO supplied | mg wt. % | 0 0 | 0 0 | 28 100 | 28 25 | 50 100 | 50 37.5 | 34 100 | 34 28.6 | 31 100 | 31 27 | 50 100 | 50 37.5 |
| inoculum (ml) | | 10 | 10 | 10 | 10 | 10 | 10 | 10 | 10 | 10 | 10 | 10 | 10 |
| buffer solution (ml) | | 90 | 90 | 90 | 90 | 90 | 90 | 90 | 90 | 90 | 90 | 90 | 90 |

EO: Essential oil or mixture of essential oils
HMTBA: bioavailable methionine in the form of 2-hydroxy-4-methylthiobutanoic acid Using the experimental design described in Table I above, curves of the volume of gas produced as a function of time are obtained, and are mostly sigmoidal.

These curves are modelled according to the following model:

$$Y = A/(1+(C/t)^B)$$

where
Y=volume of gas produced
t=time
A, B and C=parameters of the model

Using these equations, we then analyse the modelled final volume Vf (Vf=A), as well as the time for which the rate of production of gas is maximum, called Trm (this time is used as an indirect measure of the latency, which is not accessible with this model). An analysis of variance (ANOVA) is performed on these data to evaluate the effect of the item. If the probability of the treatment effect is significant, i.e. if $p<0.05$, the means are then compared by the Fisher PLSD test, which Thus, Trm of the negative control is 10.8 h. Treatment with HMTBA gives an identical Trm, which implies that HMTBA has little if any effect on the starting up of bacterial activity when it is supplied alone.

Treatment EO1 gives Trm of 13.5 h. EO1 therefore has an effect on bacterial activity.

Mixture 1 gives Trm of 19.3 h. Mixture 1 therefore has an effect on bacterial activity which goes beyond the sum of the effects of EO1 and of HMTBA separately.

Mixture 1, as well as mixtures 2 to 5 which give the same type of results, therefore display a synergistic effect on the bacterial activity measured by Trm.

Measurement of Vf is an indicator of the long-term effect of the treatment. The objective is to minimize Vf.

The items regarded as the most effective are those which minimize the final volume and, at the same time, maximize Trm.

These are mixtures 3 and 5.

TABLE II

| | | Treatment | | | | | | | | | | |
|---|---|---|---|---|---|---|---|---|---|---|---|---|
| | | Negative control | HMTBA | EO 1 | Test item 1 | EO 2 | Test item 2 | EO 3 | Test item 3 | EO 4 | Test item 4 | EO 5 | Tesst item 5 |
| Vf (ml) | Mean | 586 | 565 | 496 | 469 | 238 | 184 | 460 | 237 | 302 | 252 | 308 | 193 |
| | Standard | 17 | 21 | 41 | 18 | 34 | 17 | 9 | 48 | 113 | 18 | 55 | 8 |

TABLE II-continued

| | | Negative control | HMTBA | EO 1 | Test item 1 | EO 2 | Test item 2 | EO 3 | Test item 3 | EO 4 | Test item 4 | EO 5 | Tesst item 5 |
|---|---|---|---|---|---|---|---|---|---|---|---|---|---|
| | | | | | | | Treatment | | | | | | |
| | deviation difference | a | a | b | bc | ef | f | c | ef | d | de | d | f |
| Trm (h) | Mean | 10.8 | 10.8 | 13.5 | 19.3 | 28.6 | 46.3 | 21.5 | 39.1 | 28.9 | 35.8 | 30.8 | 37.2 |
| | Standard deviation | 0.2 | 0.2 | 0.1 | 1.8 | 1.2 | 3.1 | 4.6 | 3.4 | 0.4 | 1.3 | 1.9 | 3.1 |
| | difference | a | a | b | c | d | f | c | e | d | e | d | e |

Vf: final volume of gas produced (ml)
Trm: time for which the rate of production of gas is maximum (hour).
Test item n = EO n + HMTBA

EXAMPLE 2

The experimental conditions and parameters of Example 1 are repeated in Example 2, according to Table III below.

TABLE III

| | | Negative Control | HMTBA | EO 1 | Test Item 1 | EO 2 | Test Item 2 |
|---|---|---|---|---|---|---|---|
| | | | | | Treatment | | |
| Item | | 0 | HMTBA | EO 1 | HMTBA + EO 1 | EO 2 | HMTBA + EO 2 |
| Repetitions | | 4 | 4 | 4 | 4 | 4 | 4 |
| Dose of | mg | 0 | 83 | 0 | 83 | 0 | 83 |
| HMTBA supplied | wt. % | 0 | 100 | 0 | 84.7 | 0 | 84.7 |
| Dose of EO | mg | 0 | 0 | 15 | 15 | 15 | 15 |
| supplied | wt. % | 0 | 0 | 100 | 15.3 | 100 | 15.3 |
| Inoculum (ml) | | 10 | 10 | 10 | 10 | 10 | 10 |
| Buffer Solution (ml) | | 90 | 90 | 90 | 90 | 90 | 90 |

EO1: red thyme
EO2: tea tree
HMTBA biavailable methionine in the form of 2-hydroxy-4-methylthiobutanoic acid Results The results appear in Table IV below.

TABLE IV

| | | Negative Control | HMTBA | EO 1 | Test item 1 | EO 2 | Test item 2 |
|---|---|---|---|---|---|---|---|
| | | | | Treatment | | | |
| Vf (ml) | Mean | 542.0 | 296.2 | 226.7 | 203.1 | 319.6 | 361.1 |
| | Standard deviation | 43.9 | 28.6 | 15.5 | 15.6 | 10.8 | 41.3 |
| | Difference | a | b | b | b | b | e |
| Trm (h) | Mean | 15.3 | 20.3 | 27.7 | 33.1 | 20.2 | 24.8 |
| | Standard deviation | 1.0 | 0.7 | 1.1 | 0.8 | 0.8 | 0.8 |
| | Difference | a | b | c | d | b | e |

Vf: final volume of gas produced (ml)
Trm: time for which the gas production rate is at a maximum (hours).
Test item n = EO n + HMTBA As regards the Trm, which should be maximized, all the treatments tested (HMTBA, EO and test item) are therefore effective.

It is once again demonstrated that there is a synergistic effect between the bioavailable methionine compound, in the case in point HMTBA, and the essential oil, on the bacterial activity.

In fact, the Trm of the negative control is 15.3 h.

The HMTBA treatment gives a Trm of 20.3 h. Thus, the HMTBA therefore has an effect on the bacterial activity when it is provided alone.

The EO1 treatment gives a Trm of 27.7 h. EO1 therefore has an effect on the bacterial activity.

Mixture 1 (or test item 1), for its part, gives a Trm of 33.1 h. Mixture 1 therefore shows an effect on the bacterial activity which goes beyond the sum of the effects of EO1 and of HMTBA in isolation.

Mixture 1 and also mixture 2, which gives results of the same type, therefore show a synergistic effect.

The measurement of Vf is an indicator of the long-term effect of the treatment. The objective is to minimize the Vf.

The items considered to be the most effective are those which minimize the final volume and, at the same time, maximize the Trm.

This is mixture 1.

NB: The differences in the values of Vf and Trm between the various examples of the present application may be due to the use of various digestive contents, derived from various batches of animals. Although the rearing, the feeding and the sampling conditions are identical, the bacterial populations which set up in the intestines of livestock animals are never rigorously the same. The variations in value observed according to the examples are due to the variation in the type of flora present in the various samples.

EXAMPLE 3

The experimental conditions and parameters of example 1 are repeated in Example 3, according to Table V below.

TABLE V

| | Treatment | | | |
|---|---|---|---|---|
| | Negative Control | HMTBA | EO 1 | Test Item 1 |
| Item | 0 | HMTBA | EO 1 | HMTBA + EO 1 |
| Repetitions | 4 | 4 | 4 | 4 |
| Dose of HMTBA    mg | 0 | 83 | 0 | 83 |
| provided            wt. % | 0 | 100 | 0 | 84.7 |
| Dose of EO         mg | 0 | 0 | 15 | 15 |
| provided            wt. % | 0 | 0 | 100 | 15.3 |
| Inoculum (ml) | 10 | 10 | 10 | 10 |
| Buffer solution (ml) | 90 | 90 | 90 | 90 |

EO1: cinnamon
HMTBA: bioavailable methionine in the form of 2-hydroxy-4-methylthiobutanoic acid Results The results appear in Table VI below.

TABLE VI

| | | Treatment | | | |
|---|---|---|---|---|---|
| | | Negative Control | HMTBA | EO 1 | Test Item 1 |
| Vf (ml) | Mean | 632.7 | 334.3 | 218.3 | 20.0 |
| | Standard deviation | 23 | 86 | 82 | 10 |
| | Difference | a | b | c | e |
| Trm (h) | Mean | 14.1 | 28.1 | 53.5 | >72 |
| | Standard deviation | 0.1 | 2.2 | 10.9 | nd |
| | Difference | a | b | c | d |

Vf: final volume of gas produced (ml)
Trm: time for which the gas production rate is at a maximum (hours)
Test item n = EO n + HMTBA
nd: not determined All the compositions tested give results that are significantly different than the control with respect to the two criteria, i.e. Vf and Trm. These compositions therefore have a reducing effect on the activity of the ileal flora.

As regards the Trm, which should be maximized, all the treatments tested (HMTBA, EO and test item) are therefore effective.

It is once again demonstrated that there is a synergistic effect between the bioavailable methionine compound in the case in point HMTBA, and the essential oil, in the case in point cinnamon essential oil, on the bacterial activity.

In fact the Trm of the negative control is 14.1 h.

The HMTBA treatment gives a Trm of 28.1 h. Thus, the HMTBA has an effect on the bacterial activity when it is provided alone.

The EO1 treatment gives a Trm of 53.5 h. EO1 therefore has an effect on the bacterial activity.

Mixture 1 (or test item 1), for its part, gives a Trm of "greater than 72 h". It therefore shows a virtually complete bactericidal activity which prevented the production of gas by the bacteria derived from the digestive content. The combination of HMTBA and the cinnamon essential oil therefore has a very strong effect on the bacterial activity, which effect goes beyond the sum of the effects of the essential oil of cinnamon and of the HMTBA in isolation.

Mixture 1 therefore has a strong synergistic effect. See figure 6.

The measurement of Vf is an indicator of the long-term effect of the treatment. The objective is to minimize the Vf.

The items considered to be the most effective are those which minimize the final volume and, at the same time, maximize the Trm.

Mixture 1 corresponds to these characteristics and it can therefore be considered to be particularly effective.

EXAMPLE 4

The experimental conditions and parameters of Example 1 are repeated in example 4, according to Table VII below.

TABLE VII

| | Treatment | | | |
|---|---|---|---|---|
| | Negative Control | HMTBA | MHO | Test Item |
| Item | 0 | HMTBA | MEO2 | HMTBA + MHE2 |
| Repetitions | 4 | 4 | 4 | 4 |
| Dose of HMTBA    mg | 0 | 83 | 0 | 83 |
| provided            wt. % | 0 | 100 | 0 | 84.7 |
| Dose of EO         mg | 0 | 0 | 15 | 15 |
| provided            wt. % | 0 | 0 | 100 | 15.3 |
| Inoculum (ml) | 10 | 10 | 10 | 10 |
| Buffer solution (ml) | 90 | 90 | 90 | 90 |

MEO: ¾ tea tree and ¼ cinnamon essential oil
HMTBA: bioavailable methionine in the form of 2-hydroxy-4-methylthiobutanoic acid Results The results appear in Table VIII below

TABLE VIII

| | | Treatment | | | |
|---|---|---|---|---|---|
| | | Negative Control | HMTBA | MEO | Test Item |
| Vf (ml) | Mean | 518 | 421 | 377 | 253 |
| | Standard deviation | 35 | 37 | 21 | 2 |
| | Difference | a | b | b | d |
| Trm (h) | Mean | 11.1 | 15.4 | 19.0 | 25.3 |
| | Standard deviation | 1.4 | 1.7 | 2.7 | 2.6 |
| | Difference | a | b | d | e |

Vf: final volume of gas produced (ml)
Trm: time for which the gas production rate is at a maximum (hours).

It is once again demonstrated that there is a synergistic effect between the bioavailable methionine compound and the mixtures of essential oil on the bacterial activity.

The Trm of the negative control is 11.1 h.

As regards the test item, which consists of 84.7% of HMTBA and 15.3% of a mixture of ¾ tea tree essential oil and ¼ cinnamon essential oil:

the HMTBA treatment gives a Trm of 15.4 h. Thus, the HMTBA has an effect on the bacterial activity when it is provided alone (difference with the negative control), value of the difference: 4.3 h;

the MEO treatment gives a Trm of 19.0 h. EO1 therefore has an effect on the bacterial activity (difference with the negative control), value of the difference 7.9 h.

the mixture (or test item), for its part, gives an Trm of 25.3 h. The mixture therefore has an effect on the bacterial activity which goes beyond the sum of the effects of MEO2 and of HMTBA in isolation. Specifically, (25.3-11.1) is greater than (4.3+7.9).

The mixture therefore has a synergistic effect on the bacterial activity.

The measurement of Vf is an indicator of the long-term effect of the treatment. The objective is to minimize the Vf.

The items considered to be the most effective of those which minimize the final volume and, at the same time, maximize the Trm.

The mixture of this test corresponds to these characteristics and can therefore be considered to be particularly effective.

EXAMPLE 5

With Example 1, the effectiveness of the five mixtures of essential oils in reducing the activity of the ileal flora derived from animals fed with a wheat-based diet was shown.

The objective of this test is to demonstrate that three of these mixtures also have a reducing effect on the activity of the ileal flora derived from chickens fed with a corn-based diet.

Animals and Samples

Conditions identical to those of Example 1.

Tests In Vitro

The experimental scheme is shown in Table I for mixtures 2, 3, 4 and 5.

Results

The results appear in Table IX below.

TABLE IX

| | | Treatment | | | | |
|---|---|---|---|---|---|---|
| | | Negative Control | EO2 + HMTBA | EO3 + HMTBA | EO4 + HMTBA | EO5 + HMTBA |
| Vf (ml) | Means | 455 | 203 | 201 | 228 | 206 |
| | Standard deviation | 11.8 | 8.4 | 1.5 | 14.4 | 13.9 |
| | Difference | a | b | b | b | b |
| Trm (h) | Means | 17.1 | 30.1 | 22.1 | 28.0 | 30.3 |
| | Standard deviation | 0.68 | 1.86 | 1.18 | 0.63 | 2.20 |
| | Difference | a | d | b | c | d |

EO: Essential oil or mixture of essential oils

In the table, the values of the parameters are significantly different at the threshold of 5% when the treatments do not have any letter in common.

The four mixtures tested significantly reduce the Vf and significantly increase Trm compared to the control.

Consequently, these products are effective in reducing the activity of the ileal flora of chickens fed with a corn-based diet, both in the short term and in the long term, as was the case with the flora of chickens fed with a wheat-based diet (example 1).

These mixtures are therefore effective with the two types of diets used.

EXAMPLE 6

In Examples 1 and 5, the effectiveness of several mixtures of essential oils in reducing the activity of the ileal flora derived from meat chickens was shown. The objective of this test is to determine the effectiveness of these mixtures on the caecal flora of pigs.

Animals

Pigs were raised to the 100th day, then the content of their caecum was removed under anaerobic conditions.

Tests In Vitro

The experimental scheme is shown in Table I for mixtures 2, 3 and 4.

Results

The results appear in Table X.

In the table, the values of the parameters are significantly different at the threshold of 5% when the treatments do not have any letter in common.

TABLE X

| | | Treatment | | | |
|---|---|---|---|---|---|
| | | Negative Control | EO2 + HMTBA | EO3 + HMTBA | EO4 + HMTBA |
| Vf (ml) | Means | 430 | 265 | 344 | 412 |
| | Standard deviation | 48.0 | 2.5 | 27.4 | 17.4 |
| | Difference | ab | d | c | b |
| Trm (h) | Means | 21.1 | 23.9 | 25.8 | 25.2 |
| | Standard deviation | 0.36 | 1.25 | 2.04 | 1.30 |
| | Difference | a | bc | c | c |

EO: Essential oil or mixture of essential oils

All the mixtures tested reduce the Vf, significantly for 2 and 3, on average for 4, and significantly increase the Trm compared with the control. The mixtures are therefore effective in reducing the activity of the caecal flora of pigs, both in the short term and in the long term.

Thus, 3 mixtures function both on the flora of chickens and on the flora of pigs.

EXAMPLE 7

The objective of this test is to compare the effectiveness of at least one essential oil and of HMTBA when these compounds are provided separately in the bottles (the two products are present in a small amount in 100 ml of solution; there is therefore little direct contact between the molecules), or after having been mixed prior to them being added to the solution.

Animals

For this test, ileal flora derived from 35-day-old chickens fed with a wheat-based diet is used.

Tests In Vitro

In this test, one of the mixtures tested in Example 1 is tested. The experimental scheme is shown in Table I for mixture 2.

Results

The results appear in Table XI.

In the table, the values of the parameters are significantly different at the threshold of 5% when the treatments do not have any letter in common.

TABLE XI

| Treatment | | Negative Control | EO2 + HMTBA After mixing | EO 2 + HMTBA Separate supply |
|---|---|---|---|---|
| Vf (ml) | Means | 532 | 184 | 407 |
| | Standard deviation | 20.4 | 23.3 | 24.4 |
| | Difference | a | c | b |
| Trm (h) | Means | 14.8 | 31.3 | 19.4 |
| | Standard deviation | 0.45 | 3.31 | 0.66 |
| | Difference | a | c | a |

EO: Essential oil or mixture of essential oils

The effect of EO2+HMTBA is much greater when the two compounds are mixed before introduction into the bottle: the prior contact particularly improves the action of the compounds on the flora. One may therefore imagine that physicochemical interactions take place between the compounds, these interactions modifying their effectiveness. This confirms the synergistic effect of the mixture of a bioavailable methionine compound with at least one essential oil.

EXAMPLE 8

Animals

For this test, ileal flora derived from 35-day-old chickens fed with a wheat-based diet is used.
Tests In Vitro
The experimental scheme is shown in Table XII below.

TABLE XII

| | Treatment | | | |
|---|---|---|---|---|
| | | Negative Control | HMTBA | EO | Test Item |
| Item | | 0 | HMTBA | EO | HMTBA + EO |
| Repetitions | | 4 | 3 | 3 | 3 |
| Dose of HMTBA | mg | 0 | 113 | 0 | 113 |
| provided | wt. % | 0 | 100 | 0 | 89.7 |
| Dose of EO | Mg | 0 | 0 | 13 | 13 |
| provided | wt. % | 0 | 0 | 100 | 10.3 |
| Innoculum (ml) | | 10 | 10 | 10 | 10 |
| Buffer solution (ml) | | 90 | 90 | 90 | 90 |

EO: Origanum oil

Results

The results appear in Table XIII below. In the table, the values of the parameters are significantly different at the threshold of 5% when the treatments do not have any letter in common.

TABLE XIII

| | | Treatment | | | |
|---|---|---|---|---|---|
| | | Negative Control | HMTBA | EO | EO + HMTBA |
| Vf (ml) | Means | 407 | 353 | 300 | 224 |
| | Standard deviation | 45.1 | 17.7 | 127.6 | 1.9 |
| | Difference | a | a | a | a |
| Trm (h) | Means | 16.0 | 16.2 | 18.3 | 20.3 |
| | Standard deviation | 1.67 | 0.71 | 0.99 | 0.67 |
| | Difference | a | a | b | c |

When it is used alone, HMTBA has no significant effect on fermentation, as observed in Example 1.

The origanum oil increases the Trm by 2.3 hours on average compared to the negative control (significant effect).

The mixture of origanum oil and of HMTBA increases the Trm by 4.3 hours compared to the negative control. The effect of the mixture is synergistic on the activity of the bacterial flora. The oil and the HMTBA therefore act in synergy so as to reduce the activity of the flora in the short term.

The invention claimed is:

1. A method for lowering the activity of endogenous flora in livestock, comprising:
   administering to said livestock as a feed additive a synergistic composition of bioavailable methionine, comprising:
   a) a bioavailable methionine compound, and
   b) at least one essential oil; wherein:
   the bioavailable methionine compound (i) is present at a concentration of 15 wt % to 85 wt % in the synergistic composition having general formula (I):

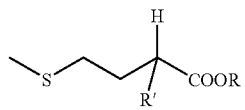

in which
R represents H or an isopropyl group and
R' represents —OH or —NH$_2$; and
   the at least one essential oil is present at a concentration of 15 wt % to 85 wt % in the synergistic composition; and
   the bioavailable methionine compound is in solution form and the essential oil is in solution form, and the bioavailable methionine compound in solution form and the essential oil in solution form are pre-mixed to form a pre-mixed solution prior to administration to the livestock; and
   the endogenous flora in livestock comprise *Campylobacter jejuni*.

2. The method of claim 1, wherein the composition further comprises:
   c) at least one other compound.

3. The method of claim 1, wherein the composition consists of:
   a) from 20 wt % to 80 wt % of the bioavailable methionine compound, and
   b) from 20 wt % to 80 wt % of the at least one essential oil.

4. The method of claim 1, wherein a feed is administered to said livestock that comprises the composition.

5. The method of claim 1, wherein the bioavailable methionine compound is 2-hydroxy-4-methylthiobutanoic acid.

6. The method of claim 1, further comprising:
   reducing livestock gas production produced by livestock intestinal microflora by at least p<0.05 when compared to at least one control and measured by a Fisher PLSD test.

7. The method of claim 6, wherein the livestock intestinal microflora comprise at least a first bacteria and a second bacteria, the first bacteria is *Campylobacter jejuni* and the second bacteria is *Salmonella* or *Clostridium perfringens*.

8. The method of claim 6, wherein the livestock intestinal microflora comprise at least a first bacteria, a second bacteria, and a third bacteria, the first bacteria is *Campylobacter jejuni*, the second bacteria is *Salmonella*, and the third bacteria is *Clostridium perfringens*.

\* \* \* \* \*